US005672107A

United States Patent [19]
Clayman

[11] Patent Number: 5,672,107
[45] Date of Patent: Sep. 30, 1997

[54] INTEGRAL VIDEO GAME AND CARDIO-WAVEFORM DISPLAY

[75] Inventor: Henry M. Clayman, Miami, Fla.

[73] Assignee: Federal Patent Corporation, Miami, Fla.

[21] Appl. No.: 594,229

[22] Filed: Jan. 31, 1996

[51] Int. Cl.$^6$ .................................. A61B 5/0444
[52] U.S. Cl. ............................. 463/36; 482/901
[58] Field of Search .................. 463/36, 30, 31, 463/7; 482/1, 901

[56] References Cited

U.S. PATENT DOCUMENTS

| Re. 34,728 | 9/1994 | Hall-Tipping | 364/413.04 |
|---|---|---|---|
| 3,765,009 | 10/1973 | Graves et al. | 345/134 |
| 3,986,498 | 10/1976 | Lewis | 128/696 |
| 3,993,861 | 11/1976 | Baer | 348/473 |
| 4,278,095 | 7/1981 | Lapeyre | 128/689 |
| 4,425,921 | 1/1984 | Fujisaki et al. | 128/690 |
| 4,889,131 | 12/1989 | Salem et al. | 128/671 |
| 5,362,069 | 11/1994 | Hall-Tipping | 463/7 |
| 5,474,082 | 12/1995 | Junker | 463/36 |
| 5,474,090 | 12/1995 | Begun et al. | 482/1 |
| 5,527,239 | 6/1996 | Abbondanza | 482/1 |

FOREIGN PATENT DOCUMENTS 2822343  11/1979  Germany.

Primary Examiner—Jessica Harrison
Assistant Examiner—James Schaaf
Attorney, Agent, or Firm—Longacre & White

[57] ABSTRACT

A video game which incorporates a video game player's cardio-waveform into the video display and integrates the wave-form with the activities of the video game being played. A cardio-waveform sensor is attached to a video game player. The sensor produces a signal which is transmitted to an input interface of a micro-processor. A joystick or other control system which enables a player to control the play of the video game is also attached to the input interface of the micro-processor. The micro-processor produces a display signal dependant on the signal's generated from the joystick and cardio-waveform sensor. The player's cardio-waveform is also displayed on the video display and is incorporated into the activities of the game being played. In one embodiment the cardio-waveform represents a boundary which confines the activities of a roaming icon.

12 Claims, 4 Drawing Sheets

INTEGRAL VIDEO GAME AND CARDIO-WAVEFORM DISPLAY

BACKGROUND OF THE INVENTION

1. Field of the Invention

The present invention is directed to a video game, and more particularly a video game which integrates a players cardio-waveform (Electrocardiogram [ECG]) into the display of the video game being played and is incorporated into the activities of the game itself.

2. Description of the Prior Art

Recent developments in computer technology have generated an explosion of video games to be played on personal computers and dedicated computer game systems to be played on home television systems. An abundance of diverse video games have been developed in the past twenty years. However, none of the video games of the prior art have integrated a video player's cardio-waveform into the video game being played.

U.S. Pat. Nos. 5,362,069 and Reissue 34,728 each disclose an exercise device comprising a video game wherein the signal representing the heart rate of the player affects the level of play of the video game and are incorporated herein by reference. However, these references fail to disclose a means to display the player's cardio-waveform nor do they incorporate this wave-form into the play of the video game.

U.S. Pat. No. 4,278,095 to Lapeyre discloses an exercise monitoring system and is herein incorporated by reference. Lapeyre '095 discloses an exercise device which simply numerically displays a person's heart rate on a TV monitor. Lapeyre '095 does not incorporate a video game nor does it display or integrate a cardio-waveform.

U.S. Pat. No. 3,765,009 discloses an apparatus for displaying a time varying waveform and is herein incorporated by reference. This reference discloses an apparatus to display a generic time varying wave-form, including a person's cardio-waveform. However, it does not involve a video game.

German Offenlegungschrift 2,822,434 discloses an exercise device wherein an exerciser's cardio-waveform is superimposed over a video display of a video tape or television broadcast. German '434 does not disclose a video game or the incorporation of a persons cardio-waveform into a video game.

The prior art does not disclose the integration of a cardio-waveform into the play of a video game, nor even the display of a person's cardio-waveform on a video game screen.

SUMMARY OF THE INVENTION

The apparatus according to the present invention comprises a computer video game which incorporates a player's cardio-waveform into the video display and effects the activities of the video game itself. A conventional computer video game system is provided comprising a micro-processor based control system, a joystick or other manual control system and a video display system. A cardio-waveform sensor is also provided to sense a player's electrocardio waveform. This sensor is attached to a player's body, either independently or in conjunction with the game controls, and produces an electrical signal indicative of the player's cardio-waveform. This signal is transmitted to the input interface to enable processing by the micro-processor. The micro-processor uses the signal from the cardio sensor and joystick to generate and transmit signals to a video controller. These signals adjust the play of the video game.

DESCRIPTION OF THE PREFERRED EMBODIMENT

Figure 1:
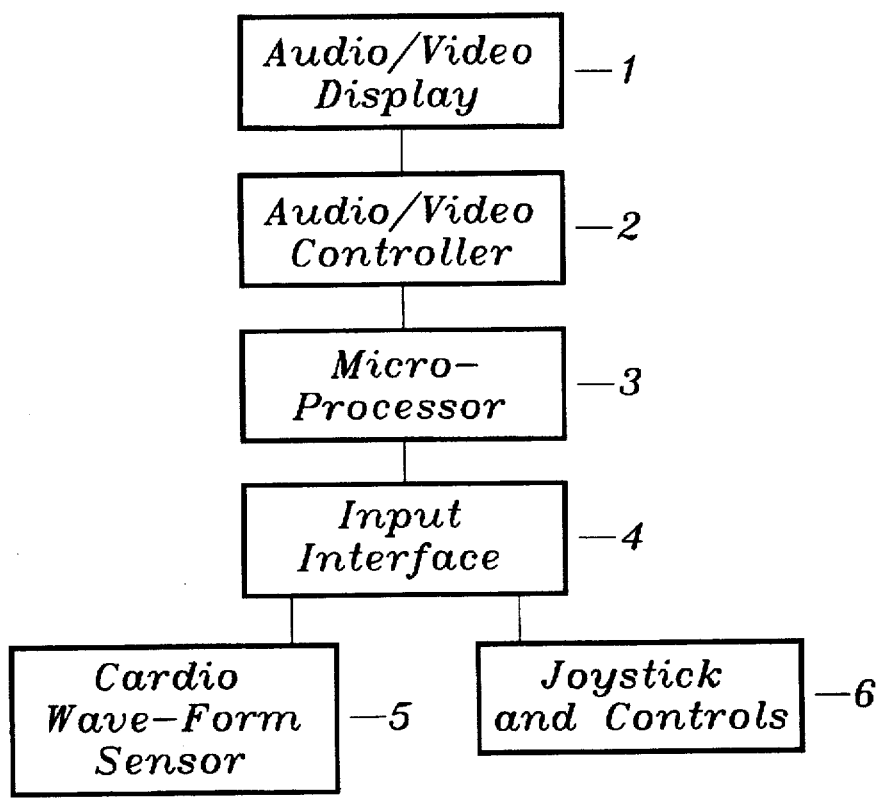
FIG. 1 is a block diagram of the video game device according to the invention with cardio-waveform and controller input devices.
Figure 2:
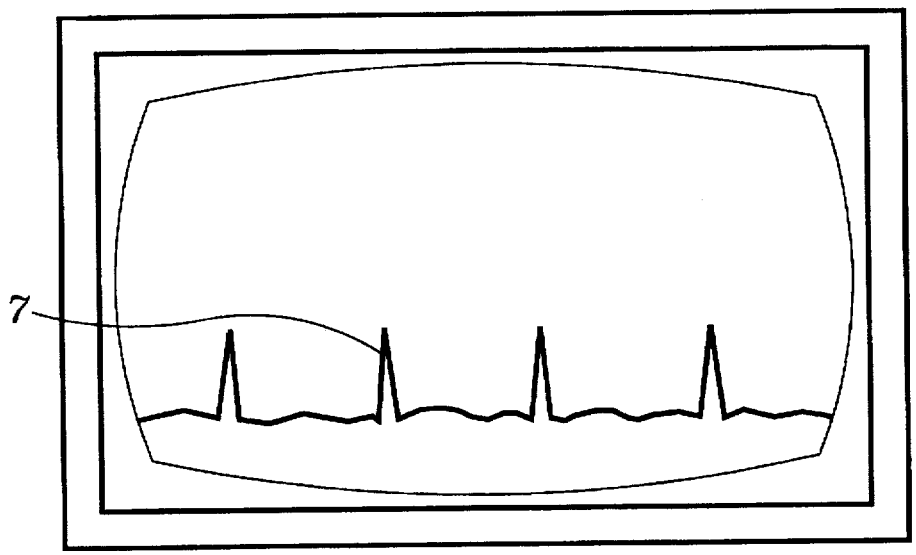
FIG. 2 is a representation of the video display illustrating the display of the time-varying cardio-waveform.

FIG. 1 is a block diagram of a video display 1, audio/video controller 2, a micro-processor 3, input interface 4, manual joystick control 6, and cardio-waveform sensor 5. Cardio-waveform sensor 5, is attached to the video game player in a suitable portion of the player's body such as the chest area or on the inside area of the player's wrist. The preferred method of attaching the cardio-waveform sensor to the player's body is to the player's wrist where the wave-form sensor 5 is embedded in a wrist band which is simply wound around the player's wrist and secured by Velcro™ or the like. In an alternate embodiment, the sensor 5, is integrally formed with the manual control device 6 such that the player's cardio-waveform is sensed by simple physical contact between the player's hands and the controls. This embodiment relieves the necessity of having a separate dedicated connection to the player's body.

The cardio-waveform sensor 5 can be of any type of the well known sensors which send signals to a conventional Electro-Cardiogram (ECG). However the cardio-waveform sensor 5 of the instant invention sends a signal, representative of the video game player's cardio-wave-form, to input interface 4.

The input interface 4 also receives a signal from a manual control device 6. The manual control device 6 can be a joystick or other conventional video game control device which generates a signal in response to a player's physical movements. The input interface then sends a composite signal to the microprocessor 3 indicative of both the player's cardio-waveform and physical manipulation of the control device 6.

The micro-processor processes the signal sent from the input interface and incorporates the cardio-waveform signal into the particular characteristics and activities of the video game being played. The microprocessor then generates an audio and a video signal which are sent to an audio/video controller 2. The audio/video controller 2 then sends a display signal to a video display which displays the video game. A wave-form 7 is displayed which not only represents the players time varying cardio-waveform but represents various characteristics of the video game being played as well. The audio/video controller also sends an audio signal to a speaker to produce sound. If the video game is to be played on a home television, a combined audio/video signal is sent to the television as conventionally found in the art.

Figure 3:
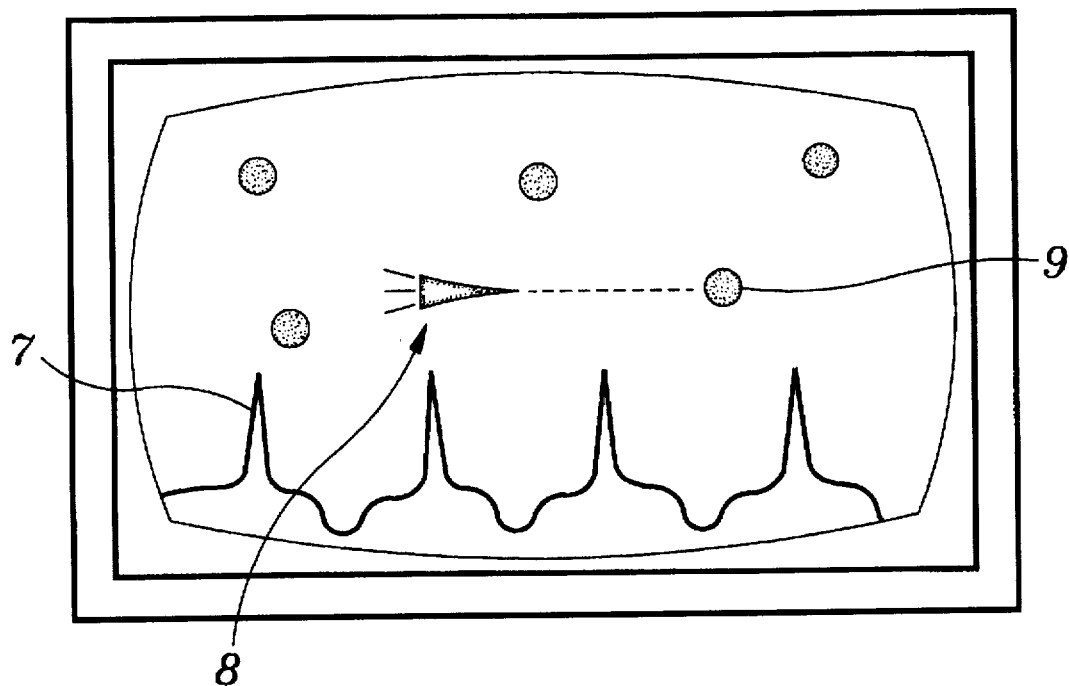
FIG. 3 is a representation of the video display illustrating the display of the time varying cardio-waveform and a video game of the first embodiment.
Figure 4:
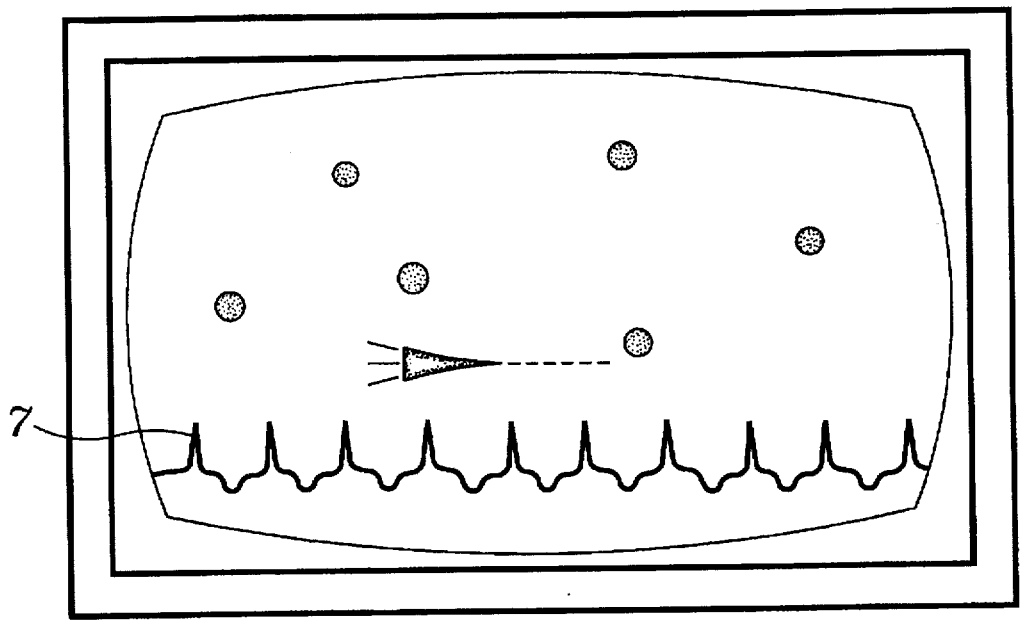
FIG. 4 is a representation of the video display illustrating the display of the time-varying cardio-waveform of increased frequency.

FIG. 3 represents one embodiment of the claimed invention where wave-form 7 represents a boundary which confines the activities of a roaming icon 8. Icon 8 can be of any type such as a space vehicle which must shoot obstacles 9 in its path or be destroyed. The movement of icon 8 is controlled by the manual control 6. In the even that the icon 8 collides with the wave-form 7, the icon is also destroyed. FIG. 4 represents the same video game as depicted in FIG. 3, however the wave form 7 has increased frequency. In the event that the players heart rate increases, due to increased challenges of the video game for example, the frequency of the player's wave-form will accordingly increase. This increased frequency will inherently provide less room for the roaming icon 8 to maneuver as the distance between the wave peaks is decreased. This will inherently pose an additional challenge to the player.

In an alternate embodiment of the claimed invention, the cardio-waveform can be altered to represent variations of the player's cardio-waveform. In one embodiment the frequency and amplitude of the waveform peaks can be increased or decreased to change the difficulty level of the game being played. The waveform displayed can vary from a pure representation of the player's cardio-waveform to a wave-form which is merely a function of the player's cardio-wave form and thus altered by the particular characteristics a specific game to be played.

Figure 5:
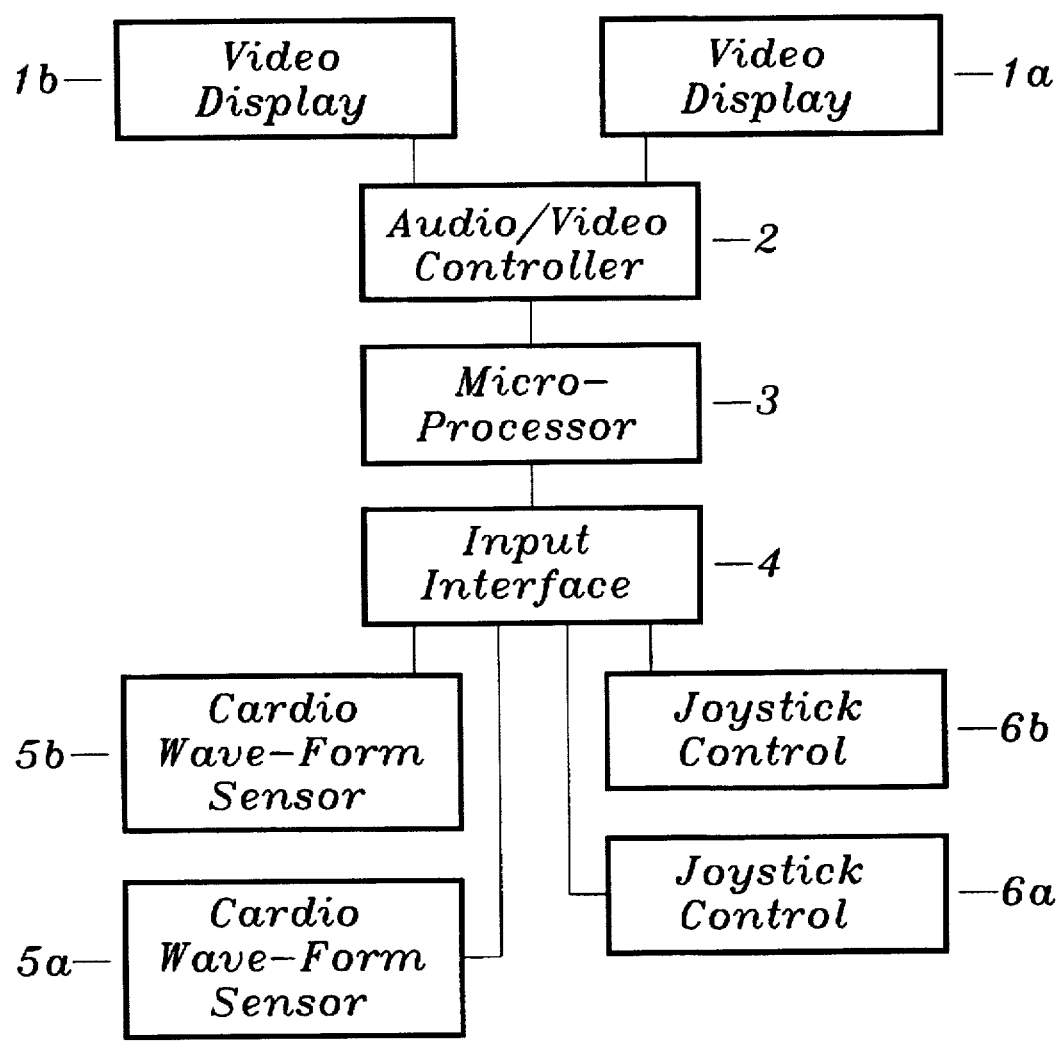
FIG. 5 is a block diagram a two player video game device according to an alternate embodiment of the claimed invention.
Figures 6A, 6B:
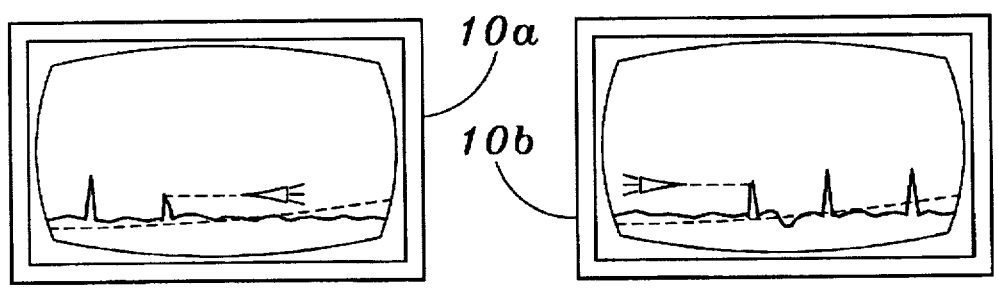
FIGS. 6a and 6b are a representation of a two player video display illustrating an alternative embodiment of the claimed invention.
Figure 7:
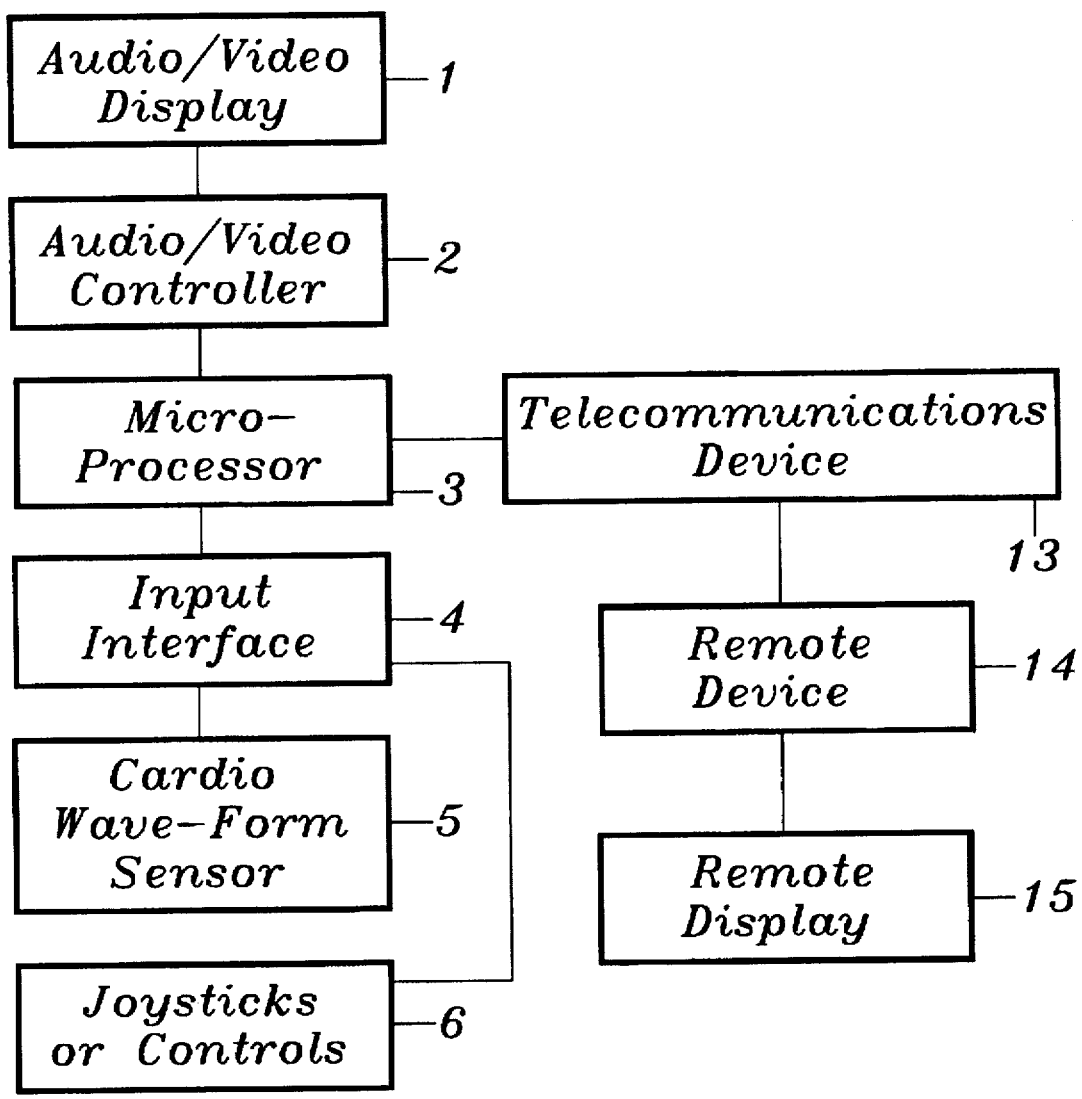
FIG. 7 is a block diagram of the video game device according to the invention with a telecommunications device.

FIG. 5, and FIGS. 6a, 6b represent an alternative embodiment of the claimed invention. FIG. 5 represents a two player game where each player controls a joystick or other conventional control device 6a, 6b. Each player also is provided with a cardio waveform sensor 5a, 5b. In the video game of this embodiment each player is provided with a video display 10a, 10b which displays their opponent's cardio waveform and their roaming icon 8. The object of the game is to shoot the other player's wave form until it is flatlined or destroyed to below a threshold level. Each player maneuvers their respective icon to shoot and destroy the opponent's wave-form. In the event one player is successful in flatlining the opponent's wave-form the other player is killed. In the event that one player is flatlined the microprocessor can generate an audio signal indicative of a flat tone sound often associated with warning sounds found on heart rate monitors which sound an alarm when a person's heart stops.

The video game of the claimed invention may either be a self contained game system to be displayed on a conventional television unit or a computer game to be played on a personal computer. In the embodiment of the self contained system, it is preferred that the input interface 4, microprocessor 3 and video controller 2 are all housed in a single console. Signals are transmitted to the input interface 4 via the manual control 6 and the cardio waveform sensor 5. The video controller then generates a signal capable of being displayed on a conventional television unit. In the personal computer embodiment, the signals from the manual control device 6, and the cardio-waveform sensor 5, are sent to the input interface which then send corresponding signals to the microprocessor of the computer through the computer's serial port. The signals are then manipulated by appropriate software and the video game is displayed by the computers video controller.

The video game of the claimed invention, may also be provided with a diagnostic mode. When the diagnostic mode is selected the sensed cardio-waveform of the player is displayed in an unaltered form. This display affords the player an opportunity to view their cardio-waveform and functions much like a conventional ECG. Information representative of normal readings may be stored in the read only memory (ROM) of the microprocessor to provide a comparative normal cardio-waveform from which to compare to the player's sensed cardio-waveform. In one embodiment the player's sensed waveform may be superimposed over the permanently stored normal waveform to facilitate diagnosis of irregularities in a player's cardio-waveform. In another embodiment, the video game can be provided with an output to send the sensed signal, representative of the player's cardio-waveform, to a telecommunications device 13 to then be transmitted to a remote device 14 for remote viewing on a remote display 15. In the event that a player self diagnoses an irregular cardio-waveform, the player may send the signal to a physician for a remote evaluation and accurate diagnosis. Such devices have currently been integrated into conventional ECGs but have not been integrated into a video game system.

The cardio-waveform 7 can be integrated into an infinite number of types of video games limited only by the creativity of a video game programmer. In an infinite number of different embodiments, the sensed waveform can be manipulated to represent a landscape or other boundry from which a player's icon, an opponents icon or other icon must traverse, or depict a surface on which a player must must try to manuever an icon against. In the embodiment where the video game is altered according to the frequency of a player's sensed cardio wave-form, indicative of a heart rate, the rate at which an opponents fuel or ammunition is replenished, the rate of an opponent's attack or other rates may be directly controlled in proportion to the sensed frequency. It is the primary purpose of the claimed invention to integrate a player's cardio waveform into the display and the activity of the video game itself. While the video game of this invention has been shown and described with reference to a particular embodiments, it will be understood to those possessing skill in the art that various changes to the form and detail may be made therein without departing from the spirit and scope of the invention.

I claim:

1. A video game having particular characteristics to be played by at least one player, said video game comprising:

a control means for allowing said at least one player to physically interact with said video game;

a means for sensing the cardio-waveform of said at least one player to produce a signal representative thereof;

a processing means for integrating said signal of said cardio-waveform into said particular characteristics of said video game;

a display means for displaying said particular characteristics of said video game with said integrated signal representative of said at least on player's cardio waveform.

2. The video game as recited in claim 1, wherein said displayed cardio wave form represents a boundary which a roaming icon cannot pass without being destroyed.

3. The video game as recited in claim 1, wherein said at least one player comprises two players each an opponent to the other;

wherein each of said at least two player's cardio waveform is sensed and displayed.

4. The video game as recited in claim 1 wherein, said means to sense said cardio-waveform of said at least one player is incorporated into said control means such that said player's cardio waveform is sensed from simple contact between said at least one player and said control means.

5. The video game as recited in claim 1 wherein, said processing means processes and alters said signal representative of said at least one player's cardio wave-form to produce a variant waveform and incorporates said variant waveform into said particular characteristics of said video game.

6. The video game as recited in claim 1, wherein said video game further comprises:

an audio means for producing sounds corresponding to said particular characteristics of said video game.

7. The video game as recited in claim 3, wherein said particular characteristics of said video game includes a roaming icon capable of shooting projectiles towards an opponents displayed cardio wave-form, the object being to flatline said opponents displayed cardio wave-form.

8. The video game claim as recited in claim 7, wherein said video game further comprises;

an audio means for producing sounds corresponding to said particular characteristics of said video game wherein when said opponents cardio waveform is flat-lined by another opponent said audio means produces a continuous flat tone.

9. The video games as recited in claim 1, wherein said video game comprises a plurality of levels of difficulty, wherein a particular level of difficulty at any point in time is dependent on the frequency of said sensed cardio waveform.

10. A video game having particular characteristics to be played by at least one player, said video game comprising:

a control means for allowing said at least one player to physically interact with said video game;

a means for sensing the cardio-waveform of said at least one player to produce a signal representative thereof;

a processing means for integrating said signal of said cardio-waveform into said particular characteristics of said video game;

a display means for displaying said video game and said cardio-waveform of said at least one player; and wherein said processing means includes a diagnostic mode for facilitating the diagnosis of an abnormally sensed cardio wave-form wherein said at least one player's cardio wave form is sensed and display unaltered.

11. A video game as recited in claim 10 wherein said displayed un-altered cardio wave-form is superimposed over a predetermined cardio wave-form.

12. A video game as recited in claim 10 wherein said diagnostic means further comprises:

a transmission means for transmitting said signal representative of said at least one player's sensed cardio-waveform to a remote location so that said signal may be displayed on a remote electrocardiogram.

* * * * *